United States Patent [19]

Kase et al.

[11] Patent Number: 4,962,125

[45] Date of Patent: Oct. 9, 1990

[54] NOVEL SUBSTANCE KS-619-1, PREPARATION PROCESS AND PHARMACEUTICAL COMPOSITION

[75] Inventors: Hiroshi Kase; Yuzuru Matsuda, both of Koganei; Kunikatsu Shirahata, Komae; Toru Yasuzawa; Koji Yamada, both of Machida, all of Japan

[73] Assignee: Kyowa Hakko Kogyo, Co., Ltd., Tokyo, Japan

[21] Appl. No.: 235,654

[22] Filed: Aug. 24, 1988

Related U.S. Application Data

[63] Continuation-in-part of Ser. No. 787,261, Oct. 15, 1985, abandoned.

[30] Foreign Application Priority Data

Oct. 15, 1984 [JP] Japan ................................ 59-215578

[51] Int. Cl.$^5$ .................... A61K 31/65; C07C 49/423; C07C 50/36
[52] U.S. Cl. .................................... 514/569; 552/201; 514/680
[58] Field of Search .......................................... 552/201

[56] References Cited

PUBLICATIONS

Chemical Abstract, vol. 109(7) #53,205w, 1987, "Microbial production of vasodilator KS-169-1".
Chemical Abstract, vol. 107(23) #214020h, 1987, Structure of a novel calcium and calmodulin-dependent cyclic nucleotide phosphodieterase inhibitor KS-619-1.
Chemical Abstract, vol. 105(9) #59955, 1980, "Vasodilator compound".
Chemical Abstract, vol. 107(21) #193918g, "KS—619—1 a new inhibitor of calcium and calmodulin", dep. cyc., nucleotide phosphodiesterase from Step. californicus.

Primary Examiner—Richard L. Raymond
Assistant Examiner—Raymond Covington
Attorney, Agent, or Firm—Michael N. Meller

[57] ABSTRACT

A novel physiologically active substance KS-619-1 having a vasodilative activity is produced by culturing Streptomyces californicus ATCC 3312.

3 Claims, 2 Drawing Sheets

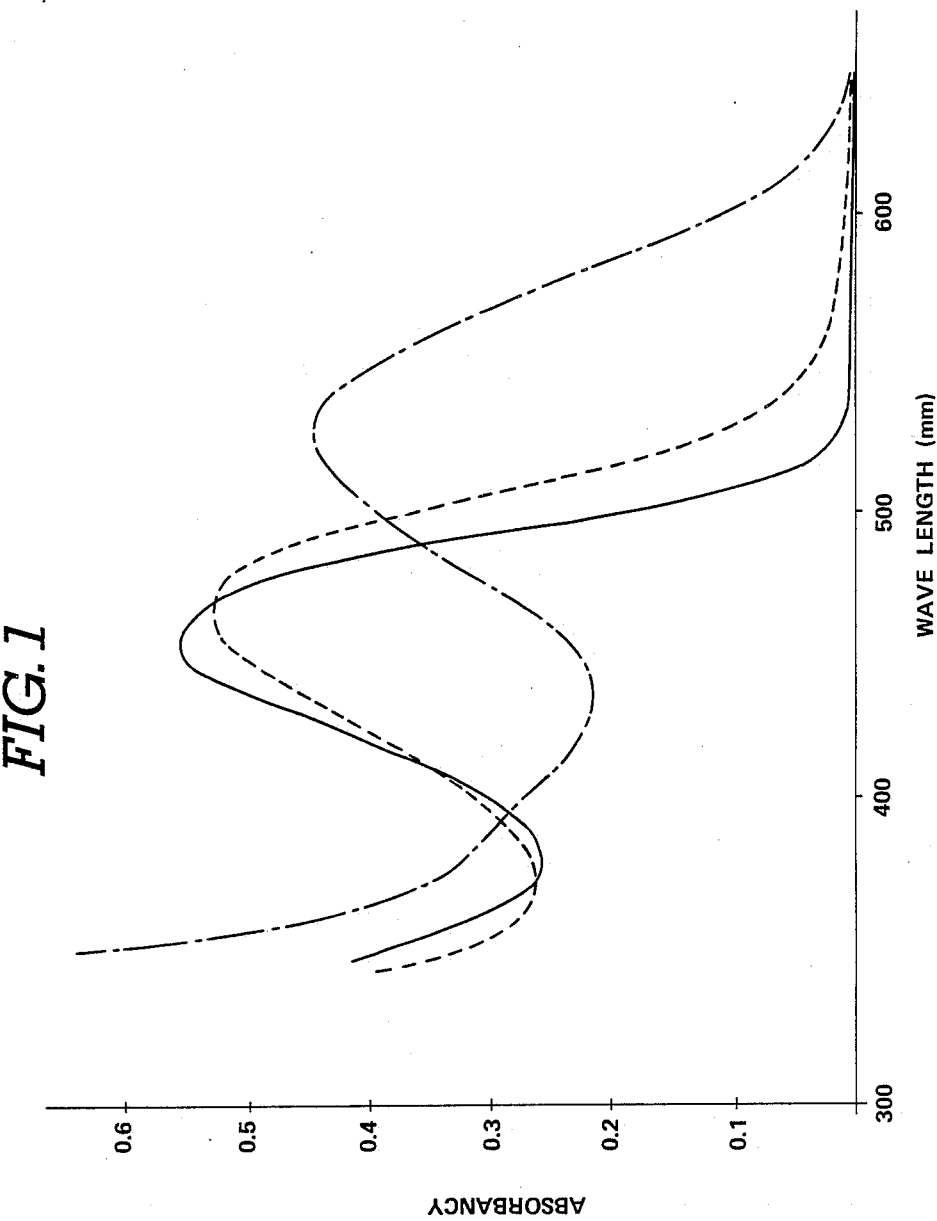

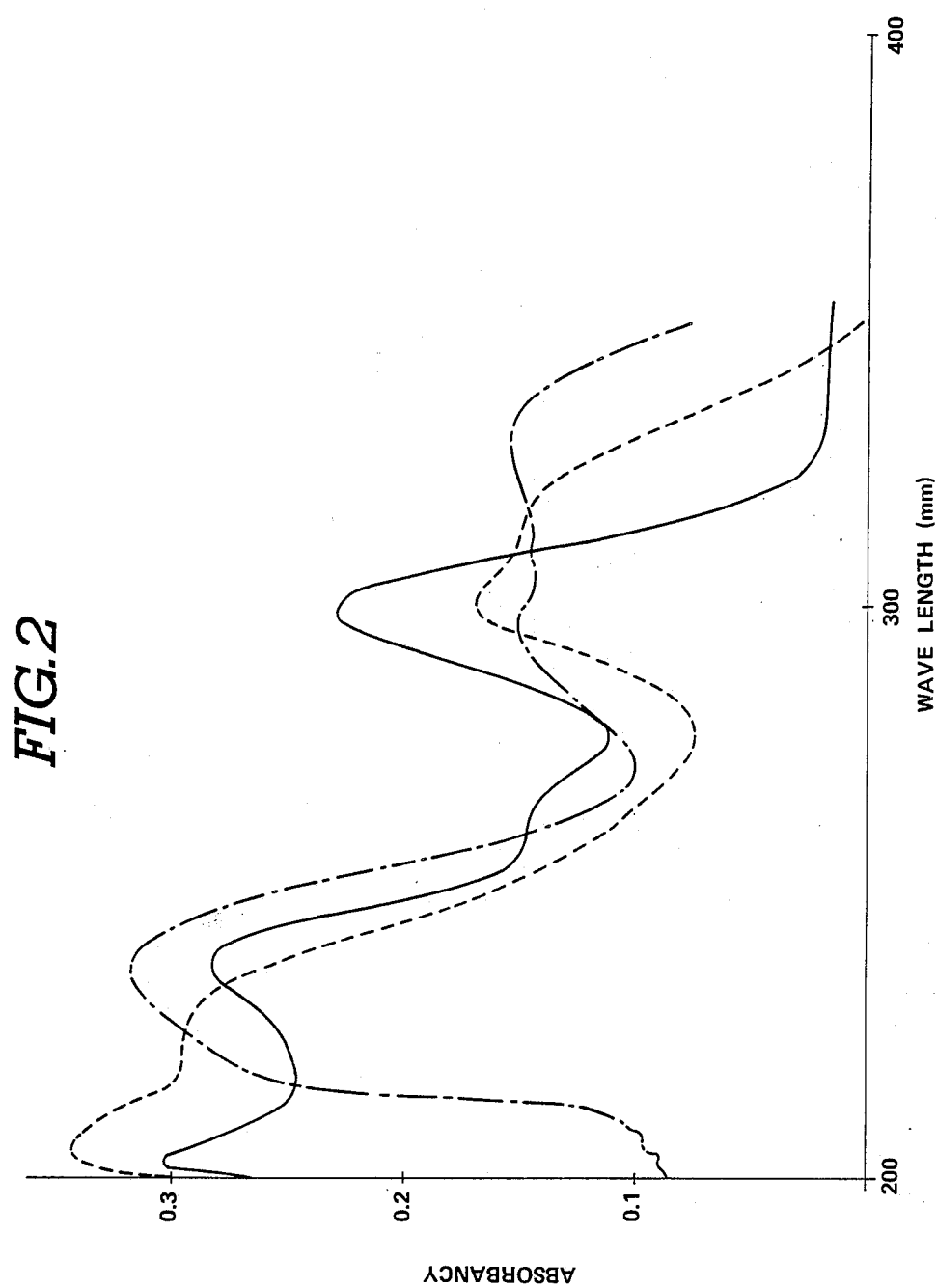

NOVEL SUBSTANCE KS-619-1, PREPARATION PROCESS AND PHARMACEUTICAL COMPOSITION

This is a continuation in part of U.S. patent Ser. No. 787,261, filed Oct. 15, 1985, now abandoned.

BACKGROUND OF THE INVENTION

This invention relates to a novel physiologically active substance produced by a microorganism belonging to the genus Streptomyces, a process for preparing the same and a pharmaceutical composition containing the same.

As a result of studies of products of a large number of microorganisms obtained from nature with a view to providing useful novel physiologically active substances, it has been found that a physiologically active substance having a vasodilative activity was produced in the culture broth of a certain microcorganism. After isolation and purification of the substance from the culture broth, its physico-chemical properties have been investigated, whereby the substance has been found to be a novel physiologically active substance. The substance is hereinafter called "KS-619-1".

As for a vasodilator produced by a microorganism, WS-1228 A and B, which are produced by culturing a strain of Streptomyces aureofaciens and have the following chemical structures, have been known [J. Antibiotics 35, 151–156 (1982), ibid. 35, 157–163 (1982)].

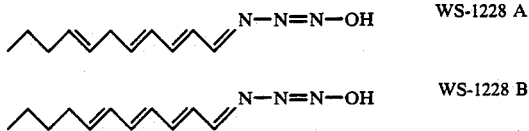

SUMMARY OF THE INVENTION

According to the present invention, a novel physiologically active substance KS-619-1 is produced by culturing a microorganism belonging to the genus Streptomyces and being capable of producing KS-619-1 in a culture medium, forming and accumulating KS-619-1 in the culture liquor, and recovering KS-619-1 therefrom. KS-619-1 has a vasodilative activity.

BRIEF DESCRIPTION OF THE DRAWINGS

FIG. 1 is absorption spectrum in the visible region of KS-619-1, wherein the solid line shows the results obtained in a 0.08N HCl - aqueous 83% (V/V) methanol solution, the dotted line in an aqueous 83% (V/V) methanol solution (neutral), and the dot-dash-line in a 0.08N NaOH - aqueous 83% (V/V) methanol solution.

FIG. 2 is absorption spectrum in the ultraviolet region of KS-619-1, wherein each line has the same meaning as above.

DETAILED DESCRIPTION OF THE INVENTION

The physico-chemical properties of KS-619-1 are given below:

State: Orange powder

Melting point: 198°–200° C. (decomposed), starting to turn brown at about 198° C. without any distinct melting point Specific rotation: $[\alpha]^2_D$ was unmeasurable because strong absorption of KS-619-1 in visible region overlapped with sodium D-line.

Solubility: readily soluble in acetic acid; soluble in methanol, ethanol, acetone, ethyl acetate and butanol; sparingly soluble in chloroform and water Color reaction: Positive in the individual reactions with ferric chloride, iodine and anisaldehyde Absorption spectrum in visible region: FIG. 1 $\lambda$max (E %): 470(339) nm in an aqueous 83% (V/V) methanol solution (neutral), 450–475(330) nm in a 0.08N HCl - aqueous 83% (V/V) methanol solution, and 390–410(250), 515(340) nm in a 0.08N NaOH - aqueous (V/V) methanol solution Absorption spectrum in ultraviolet region: FIG. 2 $\lambda$max (E%): 225(816), 302(587), 317(542) nm in an aqueous 83% methanol solution (neutral), 240(761), 265(491), 300(681), 345(236) nm in a 0.08N HCl - aqueous 83% (V/V) methanol solution, and 242(877), 298(540), 330(721) nm in a 0.08N NaOH - aqueous 83% (V/V) methanol solution Absorption spectrum in infrared region (KBr): 80, 2960, 2900, 2840, 1697, 1664, 1618, 1594, 1490, 1476, 1428, 1401, 1390, 1358, 1340, 1319, 1260, 1216, 1168, 1105, 1065, 1029, 1021, 998, 980, 921, 860, 823, 772, 757, 643, 592, 575 cm$^{-1}$ Mass spectrum: The mass spectrum of the substance gives the following ions. 457(M$^+$ $-$17, base peak), 431, 388

Molecular weight: 474

Elemental analysis: (Found) H: 3.68, C: 65.52, N: 0%. (Calculated) as $C_{26}H_{18}O_9$, H: 3.79, C: 65.82, O: 30.38, N: 0%

$^1$H-NMR spectrum (400 MHz, DMSO-d$_6$,$\delta$): 12.51 (1H, br. s), 12.17 (1H, br. s), 9.08 (1H, s), 7.15 (1H, d, J=2.2), 6.58 (1H, d, J=2.2), 6.38 (1H, s), 4.01 (2H, s), Ca. 2.8 (2H, m), Ca. 2.7 (2H, m), 2.14 (3H, s)

$^{13}$C-NMR spectrum (100 MHz, DMSO-d$_6$, $\delta$c): 189.4, 181.6, 172.3, 165.6, 164.7, 164.4, 157.8, 142.1, 141.4, 140.5, 135.4, 131.4, 130.0, 120.1, 119.9, 118.3, 116.5, 112.4, 109.0, 108.7, 107.7, 49.9, 29.8, 28.2, 20.2

Only 25 signals are observable under said $-$C-NMR measurement conditions, but in the case of a tetramethyl derivative of KS-619-1, a ketone signal is observable at 205.0 ppm.

It has been found from the foregoing data that KS-169-1 is a novel compound.

Rf values in the thin layer chromatography of KS-619-1 with various developing agents are shown in Table 1. The detection was carried out through iodine reaction.

TABLE 1

| Silica gel thin layer chromatography of KS-619-1 | |
|---|---|
| Developing solvent | Rf value |
| 1. chloroform:methanol:ethanol:water = 10:4:4:2: (V/V) | 0.48 |
| 2. n-butanol:ethanol:chloroform: ammonia water (28%) = 4:5:2:3 (V/V) | 0.33 |

Thin layer: Kiesel gel 60 (Art 5631 by Merck Co.) Development: room temperature, ascending development, one hour
KS-619-1 has a vasodilative activity.

The structural formula of KS-619-1 has been determined to be that of Formula I, below.

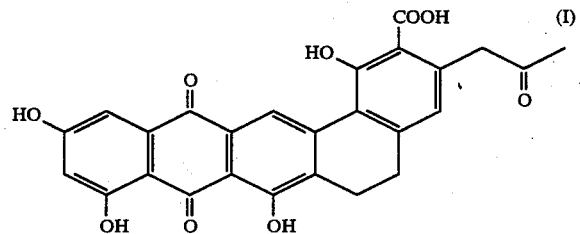

Process for preparing KS-619-1 is described below:

KS-619-1 can be prepared by culturing a microorganism belonging to the genus Streptomyces and having an ability to produce KS-619-1 in a medium, forming and accumulating KS-619-1 in the culture broth, and recovering KS-619-1 from the culture broth.

Any microorganism can be employed as a KS-619-1producing microorganism, so long as it belongs to the genus Streptomyces and has an ability to produce KS-619-1. A specifically preferable example is the strain *Streptomyces californicus* ATCC 3312, whose morphological characteristics and physiological properties are described in:

Waksman, S. A. and R. E. Curtis (1916) Soil Science, Vol. 1, pages 99–134, and

Waksman, S. A. and A. T. Henrici (1948 in Breed. R. S., E. G. D. Murray and A. P. Hitchenseds.) Bergey's Mannual of Determinative Bacteriology, Vol. 6, (The Williams and Wilkins Co., Baltimore), pages 929–980.

The ordinary culturing procedures applicable to the culturing of actinomycetes are employed to culture the microorganisms. Either a natural medium or a synthetic medium can be used, so long as it contains satisfactory amounts of a carbon source, a nitrogen source, inorganic matters, etc., which are assimilable by the microorganism.

As a carbon source, carbohydrates such as glucose, fructose, sucrose, stabilose, starch, dextrin, mannose, maltose, molasses, etc.; organic acids such as citric acid, malic acid, acetic acid, fumaric acid, etc., alcohols such as methanol, ethanol, etc.; hydrocarbons such as methane, ethane, propane, n-paraffins, etc.; amino acids such as glutamic acid, etc.; glycerol, etc. can be used.

As a nitrogen source, ammonium salts such as ammonium chloride, ammonium sulfate, ammonium nitrate, ammonium phosphate, etc.; amino acids such as aspartic acid, glutamine, cystine, alanine, etc.; urea, peptone, meat extract, yeast extract, dry yeast, cornsteep liquor, soybean meal, cottonseed cakes, soybean casein, Casamino acid, Pharma media, etc. can be used.

As inorganic materials, potassium dihydrogen phosphate, disodium hydrogen phosphate, magnesium sulfate, ferrous sulfate, manganese sulfate, cobalt sulfate, zinc sulfate, calcium pantothenate, ammonium molybdate, potassium aluminum sulfate, barium carbonate, calcium carbonate, cobalt chloride, sodium chloride, etc. can be used.

Furthermore, substances capable of promoting the propagation of cells or the production of KS-619-1 such as vitamins, thiamine, etc. can be added to the medium, if required.

When the microorganism to be used requires specific substances, it is necessary to add the substances necessary for the growth thereof.

Culturing is carried out at a temperature of 20° to 40° C. at pH around neutrality by shaking culture, aeration-stirring culture, etc.

Maximum accumulation of KS-619-1 can be attained by culturing for 3 to 15 days, and the culturing is completed.

To isolate and recover KS-619-1 accumulated in the culture broth, the ordinary procedure for the recovery of a physiologically active substance from a culture liquor can be employed.

That is, KS-619-1 can be isolated by cell removal through filtration, centrifugation, etc., and by adsorption and desorption of an active substance according to column chromatography or thin layer chromatography using adsorbing resin, silica gel, silanized silica gel, aluminum, cellulose, diatomaceous earth, magnesium silicate, gel filtration agent, etc.

One example of the process for isolating KS-619-1 from the culture liquor is given below:

Cells are removed by filtration or centrifugation of the culture liquor. The thus obtained filtrate or supernatant is treated with adsorbing resin, Diaion HP-10 (made by Mitsubishi Kasei Kogyo Co., Ltd.) to adsorb the active substance on the resin. The adsorbed active substance is eluted with an appropriate solvent such as methanol, etc., and the eluate is concentrated under reduced pressure to remove the solvent and obtain an aqueous solution. Then, a water-immiscible solvent, such as ethyl acetate, butyl acetate, etc. is added to the aqueous solution to conduct extraction.

The extract is concentrated under reduced pressure and subjected to repetitions of silica gel column chromatography to conduct purification. As a developing solvent, chloroform:methanol [=9:1 (V/V)] is initially used for the elution, and as a solvent for the successive chromatography, butanol:ethanol:chloroform:concentrated ammonia water [=4:5:2:2 (V/V)] is used for the elution. As a solvent for the third silica gel column chromatography, chloroform:methanol:ethanol:water [=10:4:4:2 (V/V)] is used for the elution. Fractions containing KS-619-1 are concentrated under reduced pressure, and the concentrate is subjected to LH-20 (product of Pharmacia Co.) column chromatography using methanol as a developing solvent. Fractions containing KS-619-1 are collected and concentrated under reduced pressure to obtain orange powders of KS-619-1.

During the said purification, detection of KS-619-1 is carried out by silica gel thin layer chromatography and then by iodine reaction.

KS-619-1 has a vasodilative activity and thus is useful as a vasodilator which is a drug capable of dilating arteries, increasing the peripheral blood flow and decreasing the overall blood pressure. That is, KS-619-1 is useful for preventing, curing or treating high blood pressure, angina pectoris, peripheral circulating insufficiency and the like. Thus, according to a further feature of the present invention, there is provided a pharmaceutical composition comprising, as active ingredient, an effective amount of KS-619-1 usually in association with at least one pharmaceutically acceptable carrier or excipient.

Dosage of these purposes depends upon the desired healing effect, way of administration, healing period, age, body weight, etc., and usually is 0.1–4 mg/kg per day for an adult as KS-619-1 through oral or parenteral route (for example, injection, application, inhalation, etc.). KS-619-1 can be administered as such, but generally administered in the form of tablets, pills, powder, granules, capsules, suppository, injection, etc. Conventional pharmaceutically acceptable carriers can be used for medical compositions of this invention. They include lactose, dextrose, sucrose, sorbitol, mannitol, glucose, cellulose, cyclodextrin, talc, starch, methylcellulose, gelatin, arabic gum, polyethylene glycol, carboxymethylcellulose, hydroxypropylcellulose, sodium benzoate, sodium hydrogen sulfite, aluminium stearate, magnesium stearate, mineral oil, vegetable oil, white vaseline, liquid paraffin, etc., and can be appropriately selected in view of the kind of preparations. The present composition can contain 0.01-85 weight percent of KS-619-1.

The acute toxicity ($LD_{50}$) of KS-619-1 in mice is more than 300 mg/kg·p.o. and more than 100 mg/kg·i.p.

The present invention is further described below, referring to examples.

EXAMPLE 1

As a seed microorganism, *Streptomyces californicus* ATCC 3312 is used, and as a first seed medium, a medium containing 1.0 g/dl glucose, 1.0 g/dl soluble starch, 0.3 g/dl meat extract, 0.5 g/dl yeast extract, 0.5 g/dl Bactotryptone (product of Difco Co.) and 0.2 g/dl calcium carbonate (pH 7.2-7.4) is used. One loopful of the seed microorganism is inoculated in 14 ml of said seed medium contained in a 50 ml-large test tube, and cultured with shaking at 30° C. for one day.

Then, 4 ml of the seed culture liquor is inoculated in 40 ml of a second seed medium contained in a 300 ml-Erlenmeyer flask. The composition of the second seed medium is the same as that of the first seed medium. The second seed culturing is carried out at 30° C. for one day. Then, 40 ml of the seed culture liquor is inoculated in 300 ml of a third seed medium contained in a 2 l-Erlenmeyer flask with baffles. The composition of the third seed medium is the same as that of the first seed medium. The third seed culturing is carried out at 30° C. for one day. Then, 900 ml of the third seed culture liquor is inoculated in 18 l of a main fermentation medium contained in a 30 l-stainless steel jar fermenter. The main fermentation medium contains 3.0 g/dl dextrin, 2.0 g/dl soybean meal, 0.25 g/dl corn steep liquor, 0.05 g/dl dipotassium hydrogen phosphate, 0.05 g/dl magnesium sulfate heptahydrate, 0.03 g/dl potassium chloride and 0.3 g/dl calcium carbonate (pH 7.8).

The culturing is carried out at 28° C. for 3 days with aeration and stirring. By means of the culturing, 0.32 µg/ml KS-619-1 is accumulated in the culture liquor. After the completion of culturing, the culture liquor is centrifuged (15,000 rpm). Then, 36 l of the supernatant is passed through a 2 l-column filled with Diaion HP-10, and after adsorption of KS-619-1, the column is washed with 6 l of 30 % (V/V) methanol, and subjected to elution with 6 l of methanol. All the eluates are collected and concentrated to 500 ml, and the concentrate is extracted with 1.5 l of ethyl acetate. The ethyl acetate layer is dehydrated over anhydrous sodium sulfate, and then concentrated to dryness, whereby 2.0 g of oily matter is obtained. The oily matter is supplied to the top of a column filled with 150 ml of silica gel (Wako gel, product of Wako Pure Chemical Co.) using chloroform. After washing with 750 ml of chloroform, the column is subjected to elution with 450 ml of a solvent, i.e. chloroform:methanol [=9:1 (V/V)]. All the eluates are collected and concentrated to dryness under reduced pressure, whereby 122.8 mg of oily matter is obtained. The oily matter is supplied to the top of a column filled with 100 ml of silica gel (Wako gel) using butanol:ethanol:chloroform:concentrated ammonia water [=4:5:2:2 (V/V)], and the column is subjected to elution with a developing solvent having the same composition as that of the filling solvent. The eluted fractions are fractionated in 7 g portions, and KS-619-1 is eluted in fraction Nos. 12–18. These fractions are collected and concentrated to dryness under reduced pressure, whereby about 70.7 mg of oily matter is obtained. The oily matter is supplied to the top of a column filled with 90 ml of silica gel (Wako gel) using chloroform:methanol:ethanol:water [=10:4:4:2 (V/V)] and the column is subjected to elution with a developing solvent having the same composition as that of the filling solvent. The eluted fractions are fractionated in 7 g portions, and KS-619-1 is eluted in fraction Nos. 2–22. These fractions are collected and concentrated to dryness under reduced pressure, whereby about 60 mg of oily matter is obtained. The oily matter is dissolved in about 5 ml of methanol, and the solution is supplied to the top of a column filled with 300 ml of Sephadex LH-20 (product of Pharmacia Co.) using methanol. Development is made with methanol, and fractions are fractionated in 5 g portions. KS-619-1 is eluted in fraction Nos. 24–57. These fractions are collected and concentrated to dryness under reduced pressure, whereby 9.7 mg of KS-619-1 is obtained as an orange powder. During the foregoing steps, KS-619-1 is detected by silica gel thin layer chromatography, and then by iodine reaction.

EXAMPLE 2

Tablets

A 10% hydroxypropylcellulose solution is added to a mixture consisting of 100 g of KS-619-1, 40g of lactose, 18 g of corn starch and 10 g of carboxymethylcellulose calcium, and the mixture is kneaded. The mixture is then granulated with an extrusion granulator with 1.0 mm screen, and the granules are dried at 60° C. The dried granules are screened on a 16-mesh sieve, and magnesium stearate is added to the granules to prepare tabletting granules. According to the ordinary procedure, tablets, 8 mm in size, containing 100 mg of KS-619-1 in one tablet (170 mg) are prepared.

EXAMPLE 3

Capsules

A 10% hydroxypropylcellulose solution is added to a mixture consisting of 50 g of KS-619-1, 80 g of lactose and 38 g of potato starch, and the mixture is kneaded. The mixture is granulated in the same manner as in Example 2, and after addition of magnesium stearate, capsules containing 50 mg of KS-619-1 in one capsule (170 mg) are prepared according to the ordinary procedure.

EXAMPLE 4

Soft Capsules

KS-619-1 (10 g) is dissolved in 100 g of soybean oil, and the solution is filled into capsules according to the ordinary procedure to prepare soft capsules each containing 10 mg of KS-619-1.

A vasodilative activity of KS-619-1 is explained below, referring to an experimental example on inhibition of contraction using extirpated blood vessel preparation.

EXPERIMENTAL EXAMPLE

(1) Preparation of surface-perfused, extirpated mesenteric arteries

White bastard rabbits (male, 2-3 kg) were incised along the abdominal median line. The superior mesenteric artery was cut out with a length of about 2-2.5 cm from the abdominal aortic branch, and spiral strips with a width of 3-4 mm were prepared therefrom. The strips were ligated with silk yarn at both ends, and the lower end was connected to a stationary rod, whereas the upper end was connected to a strong transducer (SB-1T, product of Nippon Koden Co., Ltd.). Thus, the strips were suspended under an initial tension of 1.5 g. The preparation was kept at 37°±1° C. by means of peristaltic pump (Harvard 1210), while a gas (95% $O_2$ and 5% $CO_2$) was introduced therein. The surface of the preparation was perfused with a Krebs-Henseleit solution whose composition in g/l was NaCl: 6.92, KCl: 0.35, $MgSO_4.7H_2O$: 0.29, $CaCl_2$: 0.28, $KH_2PO_4$: 0.16, $NaHCO_3$: 2.1 and glucose: 2.0 at a flow rate of 10 ml/min. After the preparation was stabilized for 1 to 2 hours, it was used for the experiment. Potassium chloride as a blood vessel-contracting substance was injected into flow of the perfusion solution through a cannula provided just before the preparation so that potassium chloride can have the ultimate concentration of 20 mM. The resulting contraction reaction was recorded on a polygraph (RM-45, product of Nippon Koden Co. Ltd.) in equal scales through the tension transducer. KS-619-1 was dissolved in ethanol to a concentration of 20 mg/ml, and the solution was properly diluted with a nutrient liquor and then continuously perfused from 10 minutes before the application of the contracting substance till the end of contraction reaction.

(2) Experimental results

TABLE 2

| Contracting substance | KS-619-1 concentration (ultimate concentration, μg/ml) | Inhibition percentage of contraction[a] (%) |
|---|---|---|
| Potassium chloride 20 mM | 0.3 | 33 |
| | 1.0 | 67 |

[a] Inhibition percentage of contraction was calculated according to the following formula.

$$\text{Inhibition percentage of contraction (\%)} = \left(1 - \frac{\text{Degree of contraction in the presence of a chemical}}{\text{Degree of contraction in the absence of a chemical}}\right) \times 100$$

As shown in Table 2, KS-619-1 inhibited the contraction of rabbit mesenteric arteries, depending on the concentration.

What is claimed is:

1. A novel substance KS-619-1 having the following physico-chemical properties:
   State: Orange powder
   Melting point: 198°-200° C. (decomposed), starting to turn brown at about 198° C. without any distinct melting point
   Solubility: readily soluble in acetic acid; soluble in methanol, ethanol, acetone, ethyl acetate and butanol; sparingly soluble in chloroform and water
   Color reaction: Positive in the individual reactions with ferric chloride, iodine and anisaldehyde
   Absorption spectrum in visible region: FIG. 1
   λmax (E %): 470(339) nm in an aqueous 83% (V/V) methanol solution (neutral), 450-475(330) nm in a 0.08N HCl - aqueous 83% (V/V) methanol solution, and 390-410(250), 515(340) nm in a 0.08N NaOH - aqueous 83% (V/V) methanol solution
   Absorption spectrum in ultraviolet region: FIG. 2
   λmax (E %): 225(816), 302(587), 317(542) nm in an aqueous 83% methanol solution, 240(761), 265(491), 300(681), 345(236) nm in a 0.08N HCl - aqueous 83% (V/V) methanol solution, and 242(877), 298(540), 330(721) nm in a 0.08N NaOH - aqueous 83% (V/V) methanol solution
   Absorption spectrum in infrared region (KBr): 3380, 2960, 2900, 2840, 1697, 1664, 1618, 1594, 1490, 1476, 1428, 1401, 1390, 1358, 1340, 1319, 1260, 1216, 1168, 1105, 1065, 1029, 1021, 998, 980, 921, 860, 823, 772, 757, 643, 592, 575 $cm^{-1}$
   Mass spectrum: The mass spectrum of the substance gives the following ions: 457($M^+$ −17, base peak), 431, 388
   Molecular weight: 474
   Elemental analysis: (Found) H: 3.68, C: 65.52, N: 0%. (Calculated) as $C_{26}H_{18}O_9$; H: 3.79, C: 65.82, O: 30.38, N: 0%
   $^1$H-NMR spectrum (400 MHz, DMSO-$d_6$, δ): 12.51 (1H, br. s), 12.17 (1H, br. s), 9.08 (1H, s), 7.15 (1H, d, J=2.2), 6.38 (1H, s), 4.01 (2H, s), ca. 2.8 (2H, m), ca. 2.7 (2H, m), 2.14 (3H, s);
   $^{13}$C-NMR spectrum (100 MHz, DMSO-$d_6$, δc): 189.4, 181.6, 172.3, 165.6, 164.7, 164.4, 157.8, 142.1, 141.4, 140.5, 135.4, 131.4, 130.0, 120.1, 119.9, 118.3, 116.5, 112.4, 109.0, 108.7, 107.7, 49.9, 29.8, 28.2, 20.2
   Only 25 signals are observable under said $^{13}$C-NMR measurement conditions, but in the case of a tetramethyl derivative of KS-619-1, a ketone signal is observable at 205.0 ppm.

2. KS-619-1, a compound of the Formula I

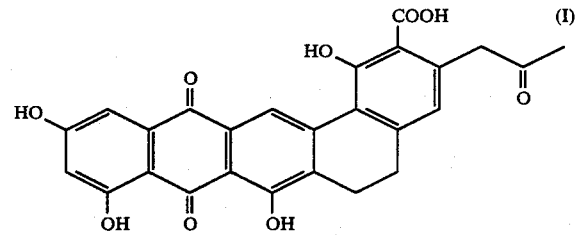

3. A pharmaceutical composition comprising as active ingredient an effective amount of KS-619-1 in association with at least one pharmaceutically acceptable carrier or excipient.

* * * * *